United States Patent
Hamdan

(10) Patent No.: US 8,451,129 B2
(45) Date of Patent: May 28, 2013

(54) PATIENT MONITORING SYSTEM WITH UNITARY STRUCTURE AND METHOD

(75) Inventor: Mahmoud N. Hamdan, Pleasant Prairie, WI (US)

(73) Assignee: Medline Industries, Inc., Mundelein, IL (US)

( * ) Notice: Subject to any disclaimer, the term of this patent is extended or adjusted under 35 U.S.C. 154(b) by 779 days.

(21) Appl. No.: 12/263,588

(22) Filed: Nov. 3, 2008

(65) Prior Publication Data

US 2010/0109879 A1    May 6, 2010

(51) Int. Cl.
*G08B 21/00*    (2006.01)

(52) U.S. Cl.
USPC .................... 340/573.1; 340/667; 600/595

(58) Field of Classification Search
USPC ............... 340/573.1, 573.4, 666, 667, 457, 340/460; 600/595
See application file for complete search history.

(56) References Cited

U.S. PATENT DOCUMENTS

| | | | | |
|---|---|---|---|---|
| 5,057,819 A | * | 10/1991 | Valenti | 340/573.1 |
| 5,063,912 A | * | 11/1991 | Hughes | 601/47 |
| 5,210,528 A | * | 5/1993 | Schulman et al. | 340/666 |
| 5,319,355 A | * | 6/1994 | Russek | 340/573.1 |
| 5,357,642 A | * | 10/1994 | Clute | 5/655 |
| 5,519,380 A | * | 5/1996 | Edwards | 340/573.4 |
| 5,675,853 A | * | 10/1997 | Linge | 5/655 |
| 6,078,261 A | * | 6/2000 | Davsko | 340/573.4 |
| 6,297,738 B1 | * | 10/2001 | Newham | 340/573.1 |
| 6,544,200 B1 | * | 4/2003 | Smith et al. | 600/595 |
| 6,549,502 B1 | * | 4/2003 | Lagasse | 369/63 |
| 7,378,975 B1 | * | 5/2008 | Smith et al. | 340/573.1 |
| 7,380,298 B2 | * | 6/2008 | Hernandez | 5/639 |
| 2001/0001237 A1 | * | 5/2001 | Stroda et al. | 340/573.4 |
| 2002/0067273 A1 | * | 6/2002 | Jaques et al. | 340/573.4 |
| 2003/0112144 A1 | * | 6/2003 | Campman | 340/573.1 |
| 2005/0187597 A1 | * | 8/2005 | Vanderschuit | 607/88 |
| 2005/0269850 A1 | * | 12/2005 | York et al. | 297/258.1 |
| 2007/0096927 A1 | * | 5/2007 | Albert | 340/573.1 |
| 2007/0210629 A1 | * | 9/2007 | Berge | 297/229 |
| 2007/0245612 A1 | * | 10/2007 | Tresenfeld | 40/665 |
| 2009/0212933 A1 | * | 8/2009 | Salazar | 340/457 |
| 2009/0294237 A1 | * | 12/2009 | Sisitsky | 190/103 |
| 2010/0073179 A1 | * | 3/2010 | Greene | 340/666 |

OTHER PUBLICATIONS

"Posey Bed", http://www.posey.com/poseystore/ProductInfo.aspx?productid=8070, Nov. 3, 2008.
"SeniorTechnologies Wander Guard", http://seniortechnologies.com/products/wanderguard/default.asp?type=longterm, Nov. 3, 2008.

(Continued)

*Primary Examiner* — Jeffery Hofsass
(74) *Attorney, Agent, or Firm* — David Noskowicz; Philip H. Burrus, IV

(57) ABSTRACT

A unitary patient monitoring system (100) includes an alarm, such as a loudspeaker (203) and a weight sensitive switch (201). Each component is encapsulated in a cover member (101), which can be configured as a T-shape. The alarm is actuated when a user removes his weight from the weight sensitive switch (201). Where the alarm is a loudspeaker (203), an audible alarm is emitted by the loudspeaker (203) when a user gets up off the unitary patient monitoring system (100). Optional features of the unitary patient monitoring system (100) include an interrupt switch (212) for temporarily rendering the alarm inactive and a master switch (211) for turning the unitary patient monitoring system (100) ON and OFF. The unitary patient monitoring system (100) can be configured to turn ON automatically when a user sits on the unitary patient monitoring system (100) as well.

19 Claims, 9 Drawing Sheets

OTHER PUBLICATIONS

"Senior Technologies TABS System", http://seniortechnologies.com/products/tabs/default.asp?type=hospital, Nov. 3, 2008.

"RFTechnologies Code Alert", http://www.rft.com/solutions/codealertwandering/, Nov. 3, 2008.

"Bed-Ex Proximity Mats", http://www.bed-ex.com/products.html, Nov. 3, 2008.

"UMP Deluxe Ultra Sentry clip alarm", http://www.horizonhcsonline.com/index.asp?PageAction=VIEWPROD&ProdID=14, Nov. 3, 2008.

"DirectSupply.net wander monitoring products", http://www.directsupply.net/dsnlogin/default.aspx, Nov. 3, 2008.

"AliMed R2 Bed Sensor Pad Alarm System and Optional Nurse Call Connection", http://www.alimed.com/ProductDetail.asp?style=70070W&fprd=TR2+Bed+Sensor+Pad+Alarm+System+and+Optional+Nurse+Call+Connection&oid1=&oid2=, Nov. 3, 2008.

"SmartCareGiver Corp. Anti-Wandering Mats", http://www.smartcaregivercorp.com/antifloormats.htm, Nov. 3, 2008.

* cited by examiner

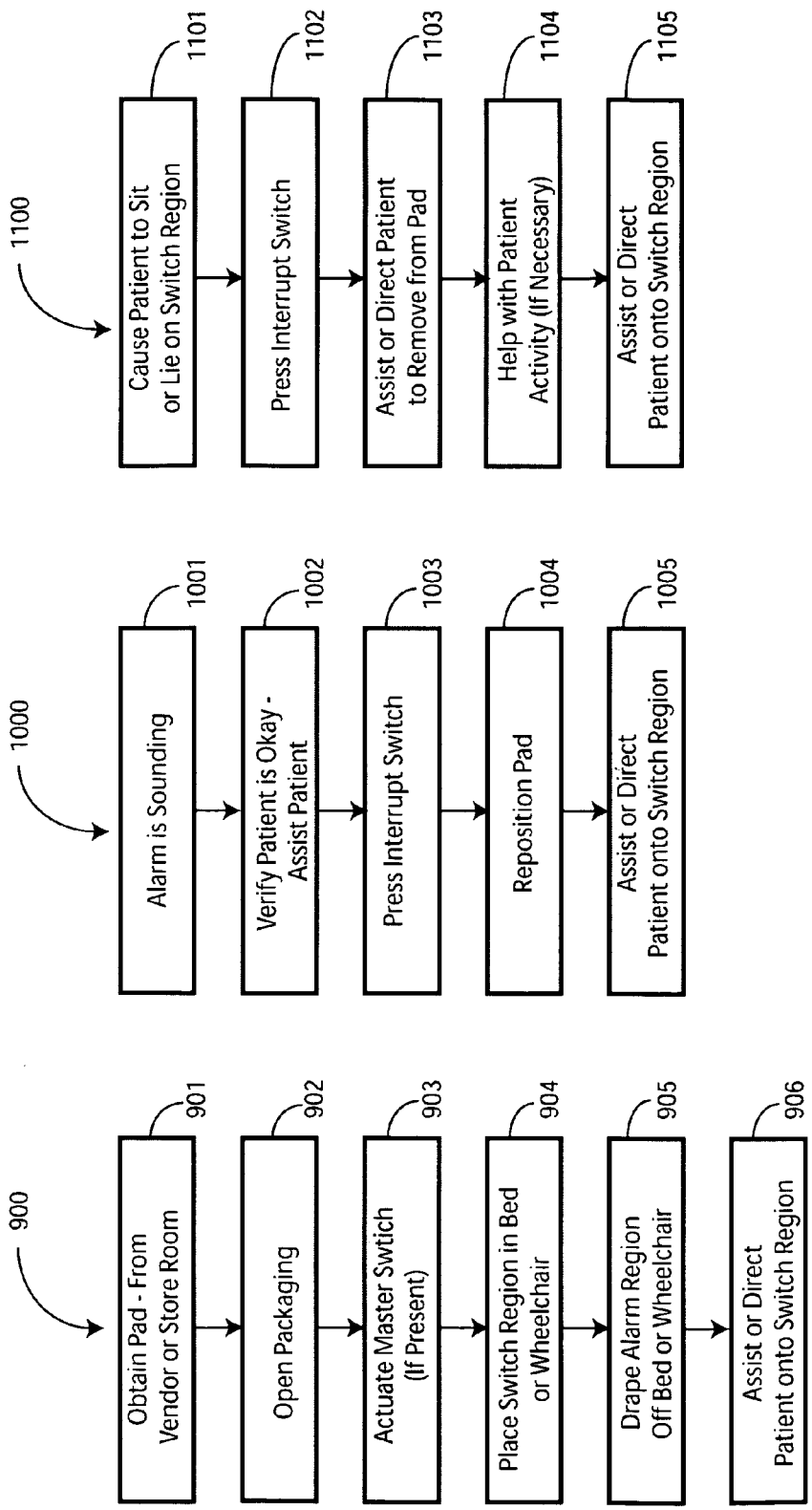

PATIENT MONITORING SYSTEM WITH UNITARY STRUCTURE AND METHOD

BACKGROUND

1. Technical Field

This invention relates generally to devices and methods for monitoring the location of a person, and more particularly to a self-contained audible alarm system, and corresponding method, that detects when a person, such as a patient in a hospital, moves from a position in a bed, wheelchair, or other furnishing.

2. Background Art

There are many situations in which a person is directed not be ambulatory. For example, a person recovering from surgery may be confined to bed rest for a predetermined amount of time. Similarly, a person recovering from a broken leg may be confined to a wheelchair until the leg sufficiently heals. Elderly patients may need the assistance of a nurse before moving on their own. Further, patients that are heavily medicated or sedated may be prone to slippage or falls, and may thus be sequestered to a bed or chair.

It can therefore be problematic when a person who should be confined to a wheelchair or bed tries to get up. They may slip and fall, thereby injuring themselves or exacerbating existing injuries. Additionally, if a patient falls out of a bed or wheelchair, they may render themselves unable to call for help. As there are generally many more patients than staff in a healthcare facility, it is often impossible to watch each patient all the time. A need exists, therefore, for a monitoring system that provides a warning to the caregiver when a patient has exited his chair or bed.

Several manufacturers have attempted to solve this problem. For instance, mechanical restraints can be used to physically confine a person to a bed or wheelchair. The problem with the use of these restraints, in addition to potentially violating patient rights and affecting patient dignity, is that the restraints may cause additional injury by binding the patient. Further, the patient in restraints may not be able to complete simple tasks such as feeding himself or changing the television channel.

Another attempt to solve the problem involves a system using magnetic tab alarms. These alarms feature a bulky control unit that is coupled to a plurality of tabs by way of tether cords. One end of the tether cord attaches to the control unit, while the other attaches to the patient's clothing. An alarm in the control unit sounds when the person moves sufficiently from the control unit as to cause the magnet or tab to dislocate from the control unit. A drawback to these systems is that they often emit false alarms as the tabs can become dislocated from simple actions such as the patient turning over. Additionally, the tether cord can become tangled with the patient's arms and legs. Next, the control unit can easily be dropped on the floor, thereby rendering it inoperable. As the control units are generally quite expensive, breakage by dropping results in significantly increased costs for the healthcare facility.

Another prior art solution involves the use of infrared light to monitor a person's location. When a person moves, infrared sensors attempt to detect this movement, thereby sending a notification signal to a remotely located control unit. The problem with these systems is that they generally must be positioned a good distance away from the patient so as to monitor the patient's full body. As such, a patient may be completely out of the bed or falling to the ground before the alarm sounds. Further, caregivers often falsely trip the infrared beams. The potential also exists for a person to defeat the system by maneuvering in a manner in which to avoid the infrared beam's detection.

There is thus a need for an inexpensive, reliable system for monitoring a person's position in a bed or chair that is reliable, resistant to breakage, not prone to nuisance tripping, and that is not easily circumvented by the person.

BRIEF DESCRIPTION OF THE DRAWINGS

FIG. 9 illustrates one method of using a patient monitoring system in accordance with embodiments of the invention.

FIG. 10 illustrates one method of using a patient monitoring system having an interrupt switch and/or autosensing actuation capability in accordance with embodiments of the invention.

FIG. 11 illustrates one method of using a patient monitoring system having an interrupt switch and/or autosensing actuation capability in accordance with embodiments of the invention.

Figure 1:
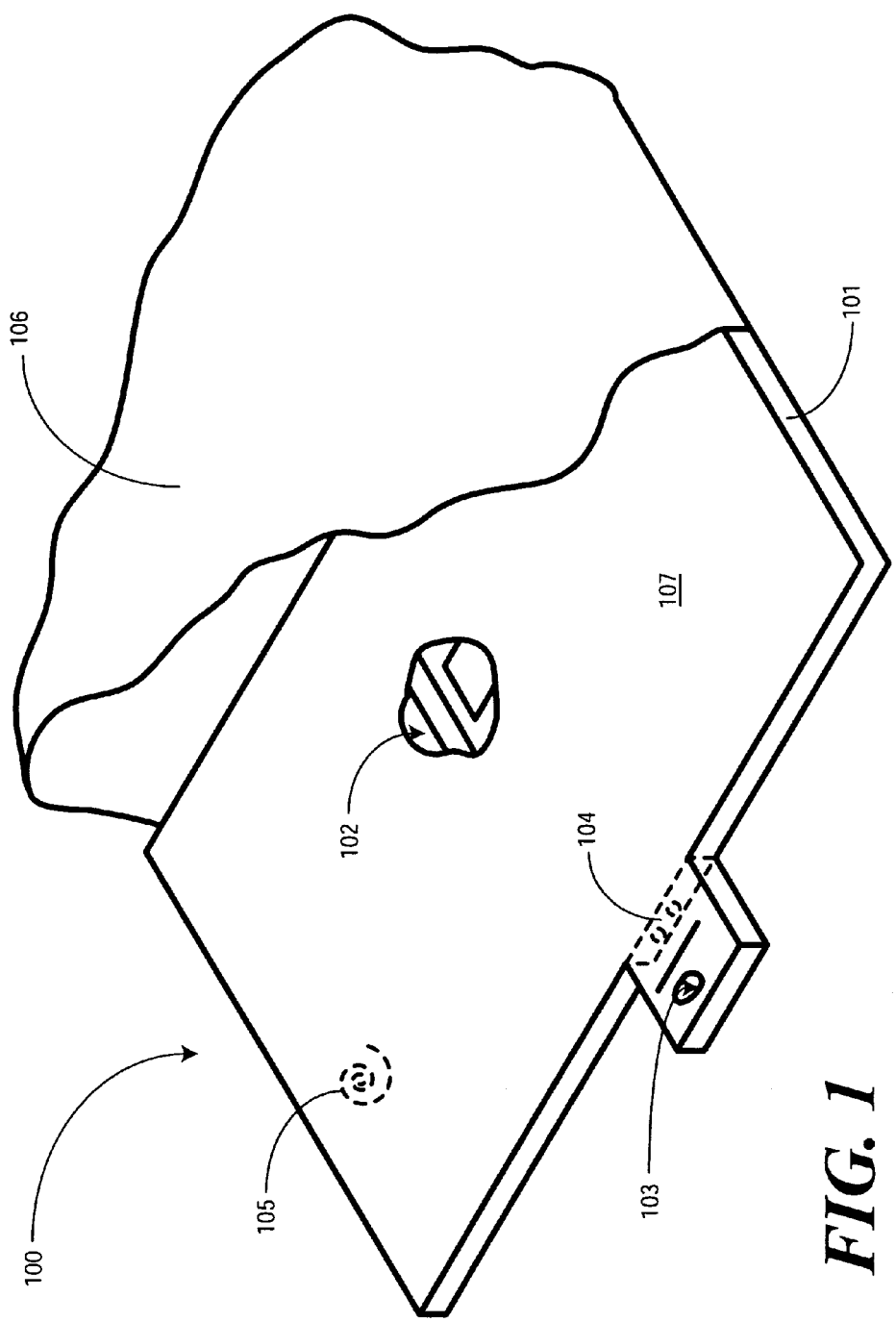
FIG. 1 illustrates one example of a unitary patient monitoring system in accordance with embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Before describing in detail embodiments that are in accordance with the present invention, it should be observed that the embodiments reside primarily in combinations of method steps and apparatus components related to monitor the position or location of a patient or person. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

As embodiments of the invention are now described in detail, referring to the drawings, like numbers indicate like parts throughout the views. As used in the description herein and throughout the claims, the following terms take the meanings explicitly associated herein, unless the context clearly dictates otherwise: the meaning of "a," "an," and "the"

includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the invention provide a unitary, pressure-sensing, system that emits an audible alarm when a person removes their weight from a weight sensitive switch. In so doing, embodiments of the invention work as a fall prevention system, alerting healthcare workers when a patient gets out of a bed or wheelchair. In one embodiment, the system incorporates a weight sensitive switch that can be configured in various sizes for bed, chair, and floor applications, and a battery powered audible alarm. Both the alarm and switch are provided as a one-piece unit, and are encapsulated by a cover member. The audible alarm broadcasts a signal to notify caregivers that a person, such as a hospital patient or nursing home resident, is either falling from a bed or wheelchair or is attempting to walk away from their bed or chair without a caregiver's assistance.

Embodiments of the present invention can be employed in situations where a caregiver, be they a skilled professional, a family member, or friend, needs assistance in determining when a patient has gotten out of a bed or chair. For example, where a person has a history of falling or is deemed to be at risk for falling is attempting to make an unassisted bed or chair exit, systems in accordance with embodiments of the invention provide advance notice of that fact.

A loudspeaker, which is operable with a weight sensitive switch, actuates when a person formerly lying or sitting on the weight sensitive switch removes their weight from the switch. The loudspeaker then provides a local, audible alarm. In one embodiment, the loudspeaker, associated control circuitry, the weight sensitive switch, and an energy source are encapsulated within a sealed cover member so as to form a "mat" or "pad." The mat can be configured in various sizes. For instance, smaller sizes accommodate the seating section of a wheelchair, while larger sizes can be used in beds. Even larger sizes can be placed on the floor if a caregiver needs to know when the person steps out of bed or a chair in an attempt to walk.

In one embodiment, the weight sensitive switch comprises electrodes disposed on opposite sides of a compliant member, such as a rubber foam separator. When a person places at least a predetermined amount of weight on the mat, the compliant member compresses, thereby allowing the electrodes to touch. Once the person removes their weight, the electrodes separate. Control circuitry, operable with the electrodes, then actuates the loudspeaker, which in one embodiment is a piezo-electric audio device. The pressure-sensitive mat is hard wired to an electronic piezo buzzer that sounds an alarm when the closed electric circuit reopens as a person removes their weight from the pressure-sensing mat. Embodiments of the invention can be provided with a master switch to turn the system on or off. Alternatively, embodiments of the invention can include an interrupt switch with which a caregiver can temporarily suspend actuation of the loudspeaker. Further, embodiments of the invention can be configured with autosensing actuation such that the loudspeaker is not capable of actuation until a patient has placed his weight upon the mat.

One advantage embodiments of the present invention offer over prior art systems is that the unitary structure provides a complete system in a one piece format. As noted above, prior art systems use multiple, separated components. These components are generally tethered together with many wires, which are cumbersome and unwieldy.

Additional benefits include that some embodiments of the present invention are disposable. Once the energy source is depleted, the healthcare provider can simply return the system to the manufacturer for another complete unit. This provides a more convenient format than having to switch out control boxes and mats as with prior art systems. Further, the absence of wires makes embodiments of the present invention more convenient for patients as there is no potential for tangling arms, legs, and clothing with the wires.

Another benefit of embodiments of the present invention is the fact that when in use, systems in accordance with the invention are not readily visible by others. As such, patient dignity is improved as no bulky control box is prominently displayed with wires tethered about the patient.

An additional advantage includes the fact that a new system may be used with each patient. Some embodiments of the invention additionally include disease and bacteria retardants, such as anti-microbial coatings. Rather than risking cross contamination between patients, as in prior art systems, embodiments of the present invention allow each patient to have a new alarm system.

Another subtle advantage is that the one-piece system makes it easier to train healthcare providers. There is no longer a need to teach the healthcare provider where to connect which wire, and so forth. Additionally, there is less risk of lost components as with multi-component systems.

Turning now to FIG. 1, illustrated therein is one embodiment of a unitary patient monitoring system 100 in accordance with the invention. In FIG. 1, the cover member 101 can be seen. The cover member 101 encapsulates and surrounds the internal components of the unitary patient monitoring system 100, which can include a loudspeaker, an energy source, weight sensitive switches, and so forth.

The cover member 101, in one embodiment, is configured to include a switch compartment 102 and an alarm compartment 103. Each compartment is a pocket or pouch that is surrounded by the cover member material. Internal components of the system are disposed within these components. For example, as will be described in more detail in FIG. 2, a weight sensitive switch may be disposed within the switch compartment 102, while control circuitry, batteries, and alarm devices may be disposed in the alarm compartment 103.

In one embodiment, the cover member 101 is configured as a T-shape. Such an embodiment is shown in FIG. 1. The T-shape works well when the unitary patient monitoring system 100 is to be used in applications such as in a bed or in the seat of a wheel chair. The alarm compartment 103 extends from the switch compartment 102 so as to form the "trunk" of the T-shape. In so doing, the patient can sit or lie atop the switch compartment 102 while the alarm compartment 103 hangs off the edge of the patient's chair or bed. In such a configuration, the alarm mechanism, which in one embodiment is a piezo-electric loudspeaker disposed in the alarm compartment 103, can freely emit an audible alarm as the alarm compartment 103 is dangling from the patient's furniture. Further, electronics disposed within the alarm compartment 103 will not be harmed when the user sits on the unitary patient monitoring system 100.

In one embodiment, the switch compartment 102 and the alarm compartment 103 meet to form a single chamber within the cover member 101. In another embodiment, the alarm compartment 103 is generally sealed from the switch compartment 102 by an optional interior wall 104. In such a configuration, the interior wall 104 can permit wires and other electronic conduit to pass through the interior wall 104, thereby linking the switches in the switch compartment 102 to circuitry in the alarm compartment 103.

The cover member 101 can be made from a single type of material or from multiple types of material. For example, the alarm compartment 103 may be made from a first material, such as a porous material configured to permit sounds waves emitted from a loudspeaker pass through, while the switch compartment 102 is made from a second material, such as a waterproof material. In another embodiment, the entire cover member 101 is made from a single material, such as a waterproof material. Certain waterproof materials, such as Gore-Tex® for example, permit more sound waves to pass through than do others, such as rubber or vinyl. Where a sound-retardant material is used about the alarm compartment 103, acoustic holes may be added to permit sound waves to pass through. Further, additional layers of the same or alternate materials may be used to ensure that moisture does not enter the alarm compartment 103 where acoustic holes are added.

In one embodiment, the cover member 101 is manufactured from a waterproof material, at least around the switch compartment 102. Using a waterproof or water resistant material can be advantageous where there is a risk of spillage or the release of bodily fluids on the unitary patient monitoring system 100. The use of waterproof or water resistant material helps to ensure that components disposed within the unitary patient monitoring system 100 do not become inoperable due to localized flooding. Further, the use of a waterproof or water resistant material helps to prevent bacteria growth within the cover member 101.

In one embodiment, the cover member 101 includes an antimicrobial coating, illustrated in FIG. 1 as dots 105. Antimicrobial coatings are designed to combat microbes and to prevent the growth or migration of bacteria. Such coatings are advantageous in that they help reduce the risk that a patient will contract a new illness while undergoing treatment. As embodiments of the present invention are unitary and disposable, the entire outer surface of the unitary patient monitoring system 100 can be treated with such a coating. Further, after each patient's use, the care giver can dispose of the system. This is advantageous when compared to prior art, multi-component systems that do not include antimicrobial coatings and that are reused from patient to patient.

Antimicrobial coatings can be applied to the outer surface of the cover member 101, or may be integrated into the material of the cover member 101 during manufacture of the material. For example, antimicrobial coatings such as those manufactured by DuPont, Inc. are offered in various colors, textures, and chemistries. Application can take the form of powder coatings that are applied to the cover member 101 and cured. Such coatings protect the cover member 101 from the growth of bacteria, mold and mildew. Examples of such coatings include U.S. Pat. Nos. 6,093,407 and 6,432,416, which are incorporated herein by reference.

In one embodiment, the cover member 101 is sealed about a perimeter of the cover member 101. As one embodiment of the unitary patient monitoring device 100 is that of a sealed, disposable unit, both the switch compartment 102 and the alarm compartment 103 can be sealed during manufacture. For example, where the cover member 101 is manufactured from vinyl, the perimeter of the cover member 101 can be sealed by a thermal weld. Where the cover member 101 is manufactured from a textile, the cover member 101 can be sealed by sewing. Alternatively, either the alarm compartment 103 or switch compartment 102 may have a sealable door that is selectively openable.

In one embodiment, a washable cover 106 is disposed about the cover member 101. The washable cover 106, which may be a different material from that of the cover member 101, is selectively removable in one embodiment. For example, while the cover member 101 may be manufactured from a waterproof material, the washable cover 106 may be manufactured from a material designed for added patient comfort, such as cotton.

In another embodiment, the cover member 101 includes a comfort component integrated therein. The comfort component can take the place of the washable cover 106, or alternatively can be used in conjunction with the washable cover 106. For example, where the cover member is manufactured from a waterproof material such as vinyl, the vinyl can have formed therein faux suede on its outer surface.

As noted above, suitable applications for the unitary patient monitoring system 100 include chairs and beds. Further, the unitary patient monitoring system 100 can be used in a wheelchair, as will be illustrated in FIGS. 5 and 6. The dimensions of the unitary patient monitoring system 100 can be configured to work in specific applications. For example, where the application of use is a wheelchair, the major faces 107 of the switch compartment 102 may measure between fourteen and eighteen inches in depth and between sixteen and twenty inches in width. In one embodiment, the major face 107 of the switch compartment 102 measures sixteen inches by eighteen inches so as to fit within the seat of a wheelchair. Other applications may require alternate dimensions. For example, when being used in a bed, the major faces 107 of the switch compartment may be extended in length and width so as to correspond to a bed width or a predetermined length of a patient's torso. In most applications, the alarm compartment 103 will be smaller than the switch compartment 102.

Figure 2:
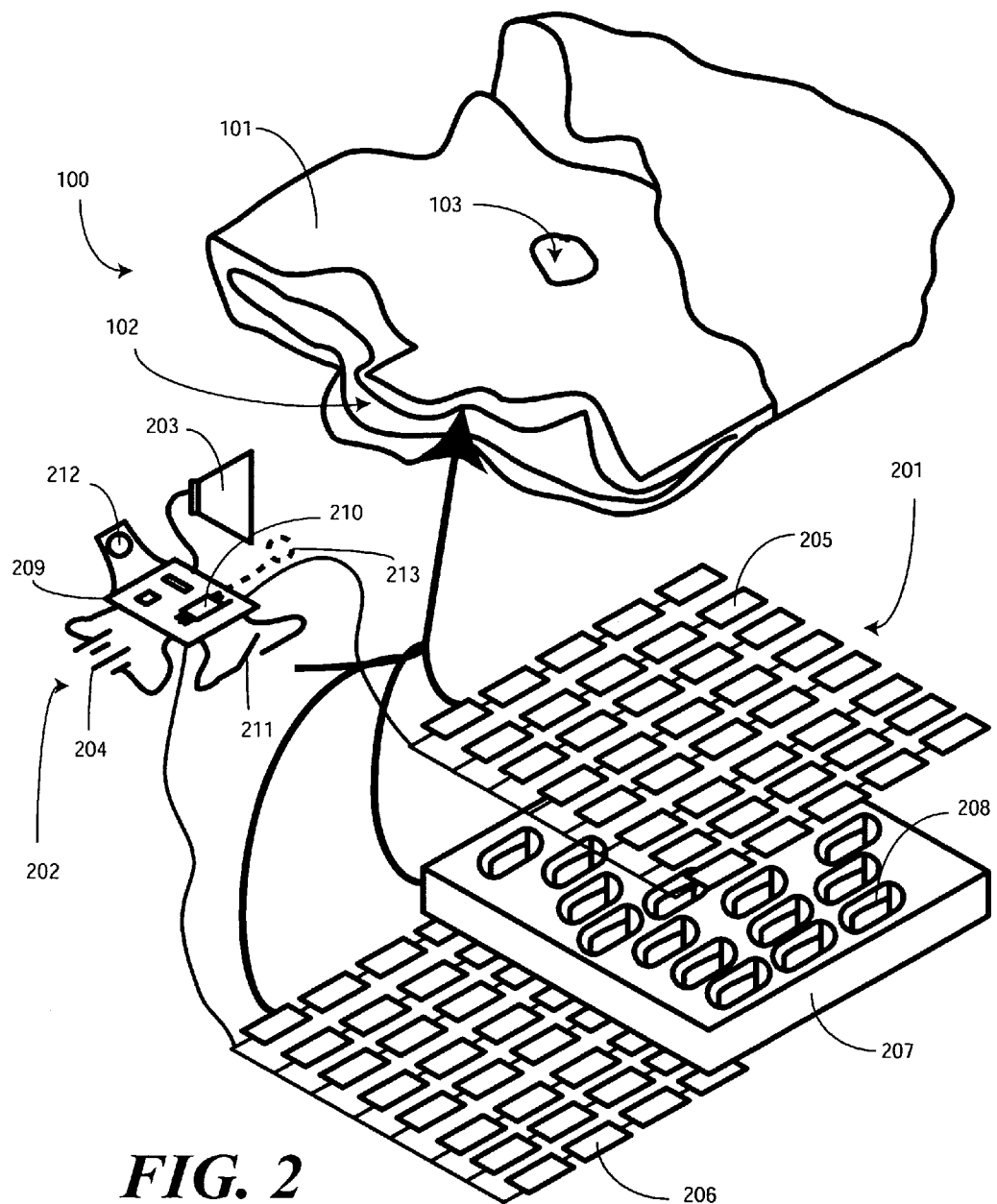
FIG. 2 illustrates an exploded view of one example of a unitary patient monitoring system in accordance with embodiments of the invention.

Turning now to FIG. 2, illustrated therein is an exploded view of one embodiment of a unitary patient monitoring system 100, configured as a patient monitoring pad, in accordance with the invention. In this view, the internal components of the unitary patient monitoring system 100 can more readily be seen. The internal components are encapsulated by the cover member 101 so as to form a single, closed outer housing about the system.

In the illustrative embodiment of FIG. 2, the internal components of the unitary patient monitoring system 100 include a weight sensitive switch 201 and corresponding circuitry 202. The circuitry 202 includes a loudspeaker 203 that is configured to emit an audible alarm upon actuation and an energy source, shown in FIG. 2 as a battery, such as a lithium, alkaline, cadmium, or nickel-metal-hydride cell. In one embodiment, the circuitry 202, including the loudspeaker 203, would be disposed within the alarm compartment 103 of the cover member 101, while the weight sensitive switch 201 is disposed within the switch compartment 102 of the cover member 101. Where the cover member 101 is configured as a T-shape, the loudspeaker 203 and circuitry 202 may be positioned in a first portion of the T-shape, such as the alarm compartment 103, while the weight sensitive switch 201 is disposed in a second portion of the T-shape, such as the switch compartment 102. Such a configuration permits the first portion of the T-shape to hang orthogonally relative to a horizontal surface supporting the patient, upon which the second portion is placed.

The weight sensitive switch 201 is illustratively shown as a first contact array 205 and a second contact array 206 separated by a layer 207 of compliant material such as rubber foam. The resilience of the compliant material is selected such that the layer 207 of compliant material is configured to permit at least portions of the contact arrays 205,206 to touch upon the application of at least a predetermined force. Requiring at least a predetermined force, such as 60 or 80 pounds, adds hysteresis to the system and prevents nuisance tripping of the alarm system.

In the illustrative embodiment of FIG. 2, the layer 207 of compliant material includes a plurality of apertures 208. When a person applies at least a predetermined force, such as 80 pounds or so, to the unitary patient monitoring system 100 by sitting or lying on the switch compartment 102, this application of force compresses the layer 207 of compliant material sufficiently that at least one contact from the first contact array 205 touches at least one contact from the second contact array 206. In one embodiment, this contact actuates the circuitry 202, thereby waking the system.

When the person removes the predetermined force from atop the switch compartment 102, the layer 207 of compressible material expands, thereby separating the contacts that were formerly touching. The circuitry 202 detects this separation and actuates the alarm, which in FIG. 2 is a loudspeaker 203. As such, the weight sensitive switch 201 is configured to actuate the loudspeaker 203 when the person's weight is removed from the system. The audible alarm tells a caregiver that the person is no longer sitting or lying on the unitary patient monitoring system 100. In one embodiment, the intensity of the audible alarm is sufficient such that a caregiver down the hall or in another room will be altered to the patient's move. Experimental research has shown that an audible alarm of between 70 and 100 decibels is generally sufficient for this purpose.

While the weight sensitive switch 201 is shown illustratively in FIG. 2 as two contact arrays 205,206 separated by a layer 207 of compressible foam, it will be clear to those of ordinary skill in the art having the benefit of this disclosure that the invention is not so limited. Other weight sensitive switch technologies can also be used, including force sensing resistor arrays or capacitive sensing technologies.

The circuitry 202, in one embodiment, includes at least an alarm and an energy source. For example, in a simple embodiment, the circuitry 202 may simply be a loudspeaker 203, an energy source such as battery 204 coupled to the loudspeaker 203, and the weight sensitive switch 201 coupled between the energy source and the loudspeaker 203. Upon application of a person's weight, and successive removal from, the unitary patient monitoring system 100, the making and braking of the circuit due to the compression of the layer 207 of compliant material and the resulting contact connection/parting can actuate the alarm.

In such a simple embodiment, a manufacture may desire to include a master switch 211. For instance, a caregiver may wish to disable the unitary patient monitoring system 100 while taking a bath. As the alarm is actuated when the patient rises from the pad, the caregiver may wish to disable the alarm through actuation of the master switch 211. To accommodate, in one embodiment, the master switch is coupled between the loudspeaker 203 and the energy source (cell 204). When the master switch 211 is in a first position, the loudspeaker 203 is capable of actuation. When the master switch 211 is in a second position, the loudspeaker 203 is incapable of actuation. In one embodiment, the master switch 211 is encapsulated within the cover member 101. A slider switch, having a tactile feel through the cover member 101, is one example of a suitable master switch device for such a configuration.

In another embodiment, no master switch 211 will be used. The unitary patient monitoring system 100 in such an embodiment will rather be "self sensing," in that the system is actuated when a person applies their weight to the system, rather than by actuation of a master switch 211. Such configurations will generally include control circuitry 209.

In another embodiment, control circuitry 209, which can include a processing circuit 210 such as a microprocessor or programmable logic, can be configured to be operable with the weight sensitive switch 201. For instance, the control circuitry 209, through embedded executable code or programmed logic, can be configured to actuate the loudspeaker 203 only upon application of, and successive removal, of at least a predetermined weight from the unitary patient monitoring system 100. Further, the control circuitry 209 can be configured with the self-sensing feature that activates the system upon application of the person's weight to the switch compartment 102.

Where control circuitry 209 is used, additional features can be added as well. For example, the control circuitry 209 can be configured to emit the audible alarm only for a predetermined duration or time period. The control circuitry 209 can be configured to emit the audible alarm for three, five, or ten minutes, for instance, upon removal of the person's weight from the unitary patient monitoring system 100. Another suitable time period may be longer, such as between fifteen and sixty minutes. Alternatively, the control circuitry 209 can be configured to emit the audible alarm until the predetermined weight is again applied to the weight sensitive switch 201.

Another feature that can be added is delayed alarm sounding. There are applications, for example, where a caregiver may wish to have the alarm sound only after a person has been off the unitary patient monitoring system 100 for some predetermined amount of time, such as 10 seconds. In such a scenario, the control circuitry 209 can be configured to actuate the alarm only after this predetermined time has lapsed.

To accommodate the situation where a caregiver wants to temporarily disable the alarm, such as for giving the patient a bath, in one embodiment the control circuitry 209 includes an interrupt switch 212 that is operable with the control circuitry 209 or processing circuit 210, where one is used. In such a configuration, the control circuitry 209 can be configured to prevent the loudspeaker 203 from emitting the audible alarm upon actuation of the interrupt switch 212 until at least the predetermined weight is applied to, and removed from, the unitary patient monitoring system 100 once again after actuation of the interrupt switch 212. This is best illustrated by way of example: A caregiver may desire to give a patient a bath. The patient gets up, thereby causing actuation of the alarm. The caregiver then actuates the interrupt switch 212, thereby quieting the alarm. Once the patient returns and places his weight on the system, the system is actuated once again. When the patient gets up, the alarm sounds. Further, the caregiver may wish to press the interrupt switch 212 prior to the patient getting up. In so doing, the caregiver prevents the alarm from actuating, thereby reducing noise and confusion in the surrounding area.

In one embodiment, the control circuitry 209 can be configured to provide a nurse call alert in addition to sounding the audible alarm. In such a configuration, an optional port 213 is provided for connecting the unitary patient monitoring system 100 to a nurse call alert system, such as those found in hospitals and other care facilities. In this embodiment, when the alarm sounds, the control circuitry 209 is configured to deliver the nurse call alert at the same time.

Figure 3:
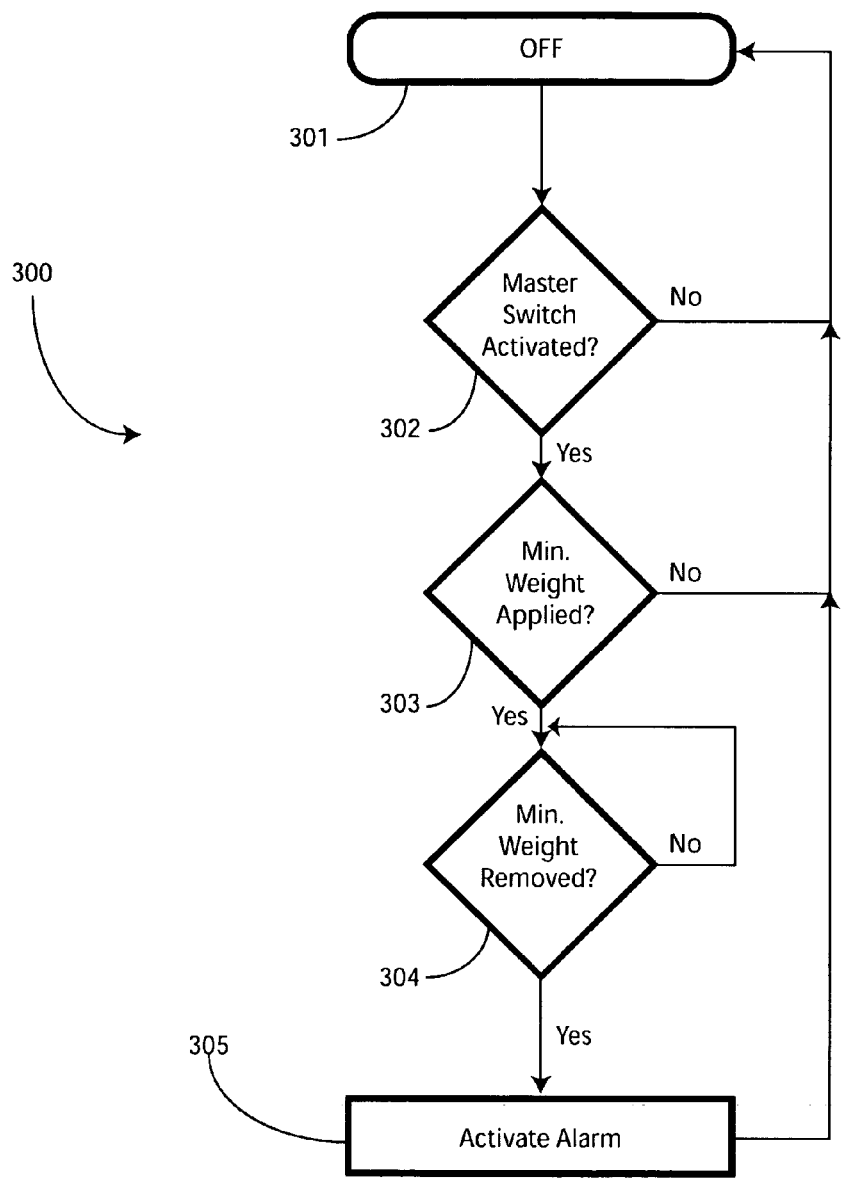
FIG. 3 illustrates one example of patient monitoring system operation, such as may be suitable for coding in firmware or configuring mechanically, in accordance with embodiments of the invention.
Figure 4:
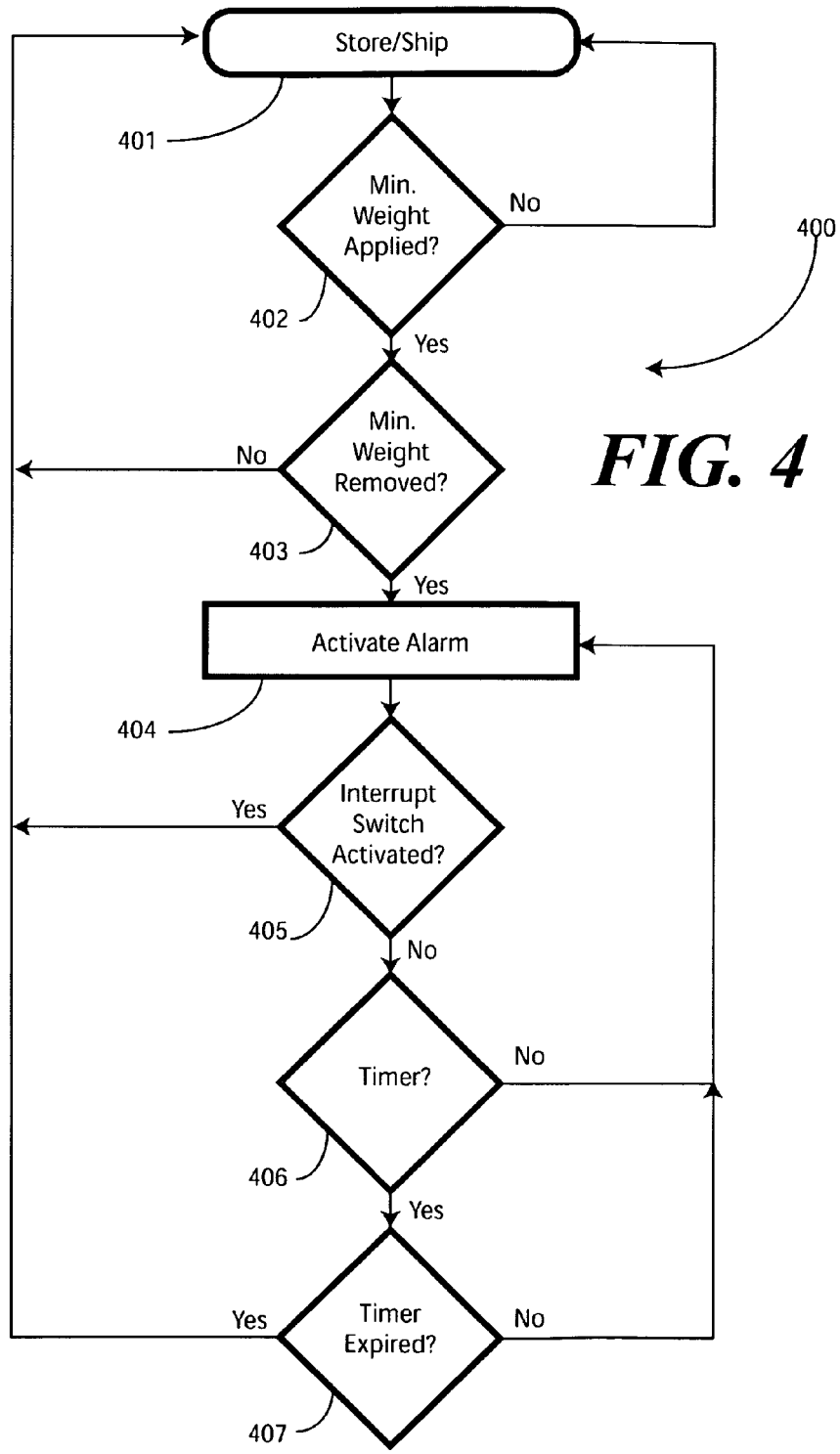
FIG. 4 illustrates another example of patient monitoring system operation, such as may be suitable for coding in firmware or configuring mechanically, in accordance with embodiments of the invention.

Turning now to FIGS. 3 and 4, illustrated therein are methods of operation of a unitary patient monitoring system (100) in accordance with embodiments of the invention. Such methods are suitable for configuration as executable code that is operable with the processing circuit 210 or control circuitry 209, or that works as programmed logic in the same. Alternatively, the methods can be configured in state machines or in hardware configurations.

FIG. 3 illustrates a method 300 associated with an embodiment of a unitary patient monitoring system (100) employing a master switch (211). At state 301, the unitary patient monitoring system (100) is OFF. A caregiver actuates the system by toggling the master switch (211) from a first position to a second position, which is detected at decision 302.

Where the master switch (211) is on, the system determines whether a predetermined weight, such as 40, 60, or 80 pounds, has been applied to the system via the weight sensitive switch (201) at decision 303. Where this is the case, the system monitors the weight, detecting its removal at decision 304. Upon removal of the predetermined weight, the system sounds the audible alarm at step 305.

FIG. 4 illustrates a method 400 associated with an alternative embodiment of the unitary patient monitoring system (100) employing an interrupt switch (212) and the auto-activation feature of the control circuitry (209).

At state 401, the system is idle, as the interrupt switch (212) has been actuated. This state is suitable for shipping the unitary patient monitoring system (100) or initially storing the unitary patient monitoring system (100).

At decision 402, the control circuitry (209) detects whether a predetermined weight has been applied to the unitary patient monitoring system (100). Where it has, the system becomes active.

At decision 403, the control circuitry (209) detects whether the predetermined weight has been removed from the unitary patient monitoring system (100). Where it has, the alarm is actuated at step 404. A caregiver can silence the alarm by actuating the interrupt switch, which is detected at decision 405. In some situations, the patient may even silence the sounding alarm by actuating the interrupt switch, such as when they momentarily rise and sit or lie back down.

In some embodiments, as mentioned above, the control circuitry (209) can be configured to emit the audible alarm only for a predetermined duration. Where a system includes this feature, the presence of a timer is determined at decision 406, and its expiration at decision 407. Where the system does not include this feature, these decisions will be omitted.

Upon actuation of the interrupt switch (212), the alarm will remain incapable of actuation until the application of, and removal of, a predetermined weight as detected at decisions 402, and 403, respectively.

Figure 5:
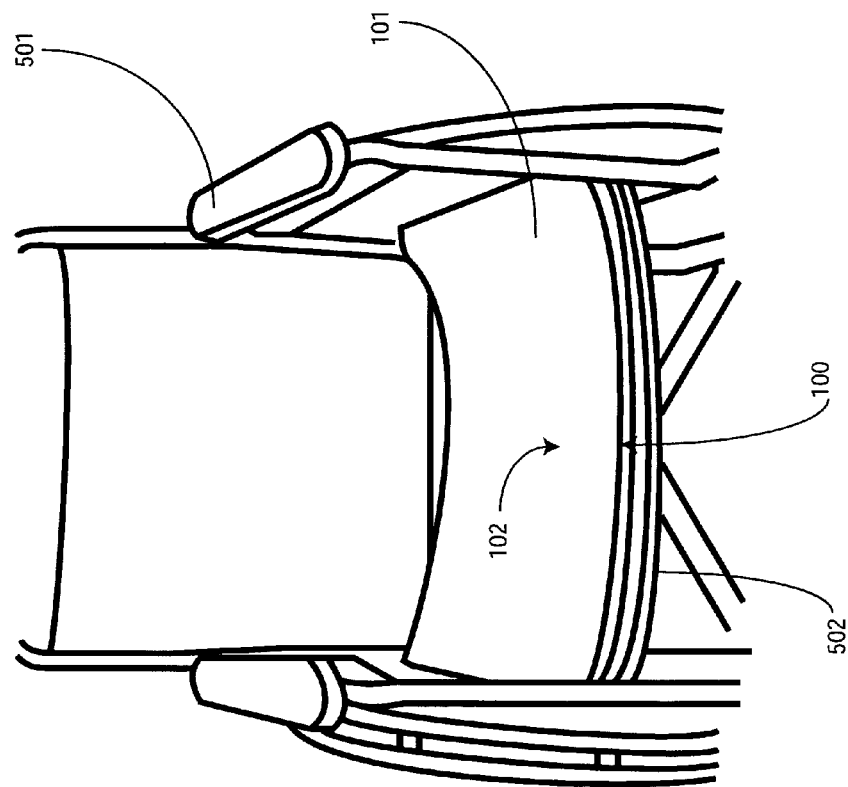
FIGS. 5 and 6 illustrate one illustrative application for a patient monitoring pad in accordance with embodiments of the invention.
Figure 6:
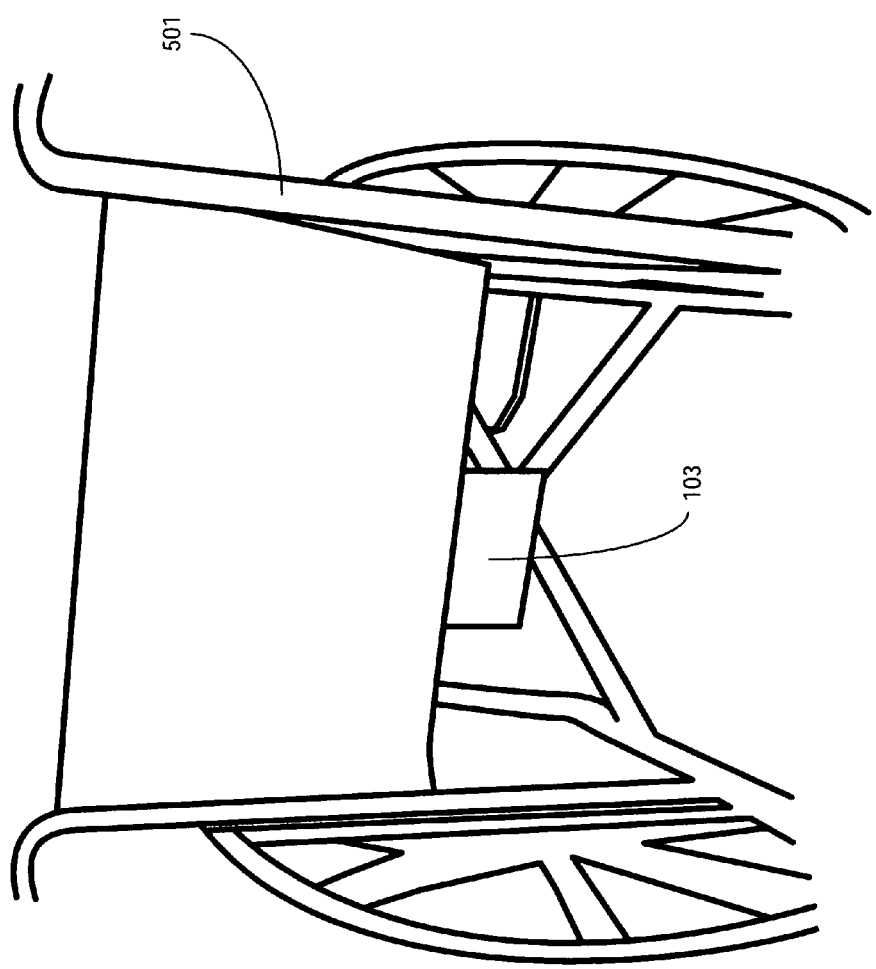

Turning now to FIGS. 5 and 6, illustrated therein is one application for a unitary patient monitoring system 100 in accordance with embodiments of the invention. The application illustrated in FIGS. 5 and 6 is that of an alarm to let caregivers know when a person has exited a wheelchair 501. In such a configuration, the unitary patient monitoring system 100 is configured in shape and size to match the seat 502 of the wheelchair 501. For example, the unitary patient monitoring system 100 may have a switch compartment 102 that is generally rectangular in shape and measures roughly 16"×18" so as to fit within the seat 502 of a standard wheelchair 501.

As shown in FIGS. 5 and 6, the cover member 101 of the unitary patient monitoring system 100 is substantially T-shaped. A first portion of the T-shape, shown in FIG. 5 as the switch compartment 102, is placed within the seat 502 of the wheelchair 501. A second portion of the T-shape, shown in FIG. 6 as the alarm compartment 103, can then hang down from the seat 502 behind the wheelchair 501. As such, the alarm operates as an integral part of the unitary patient monitoring system 100 with the alarm away from and behind the patient. Further, the caregiver has access to the alarm compartment 103 without having to move the patient.

Figure 7:
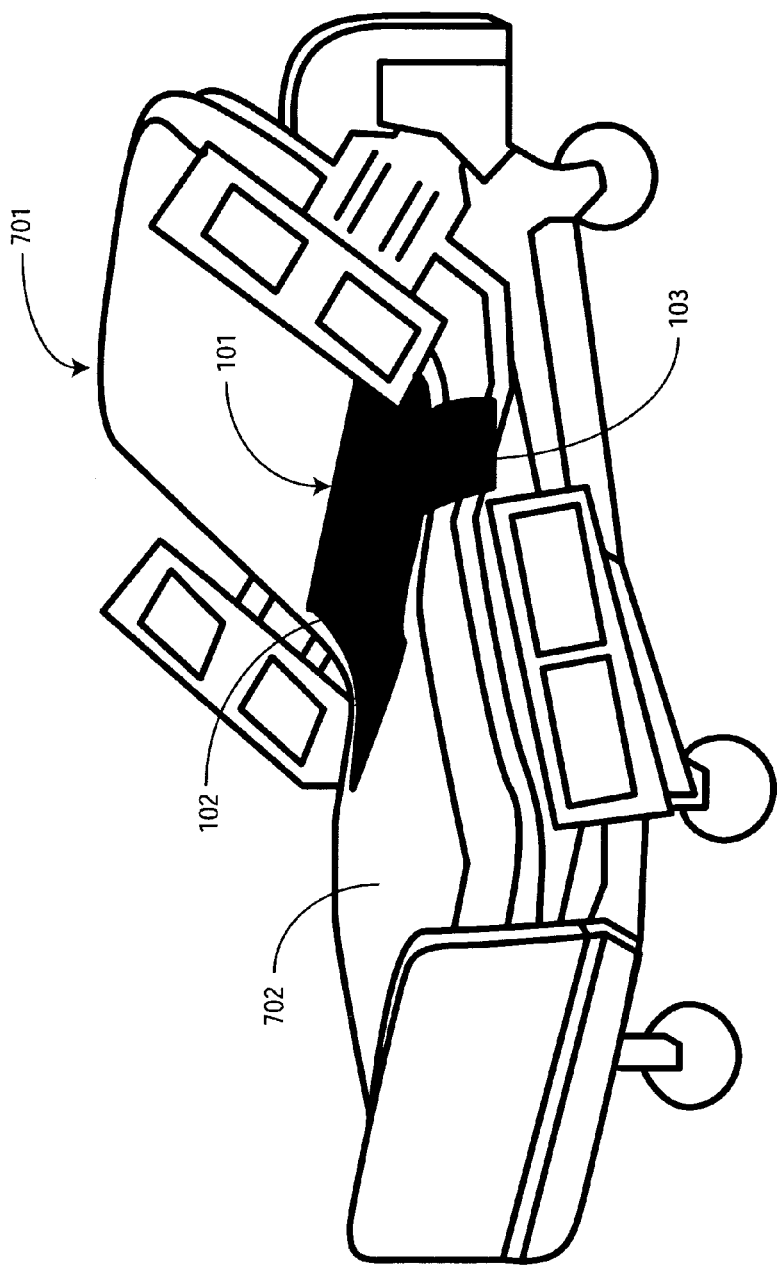
FIGS. 7 and 8 illustrate one illustrative application for a patient monitoring pad in accordance with embodiments of the invention.
Figure 8:
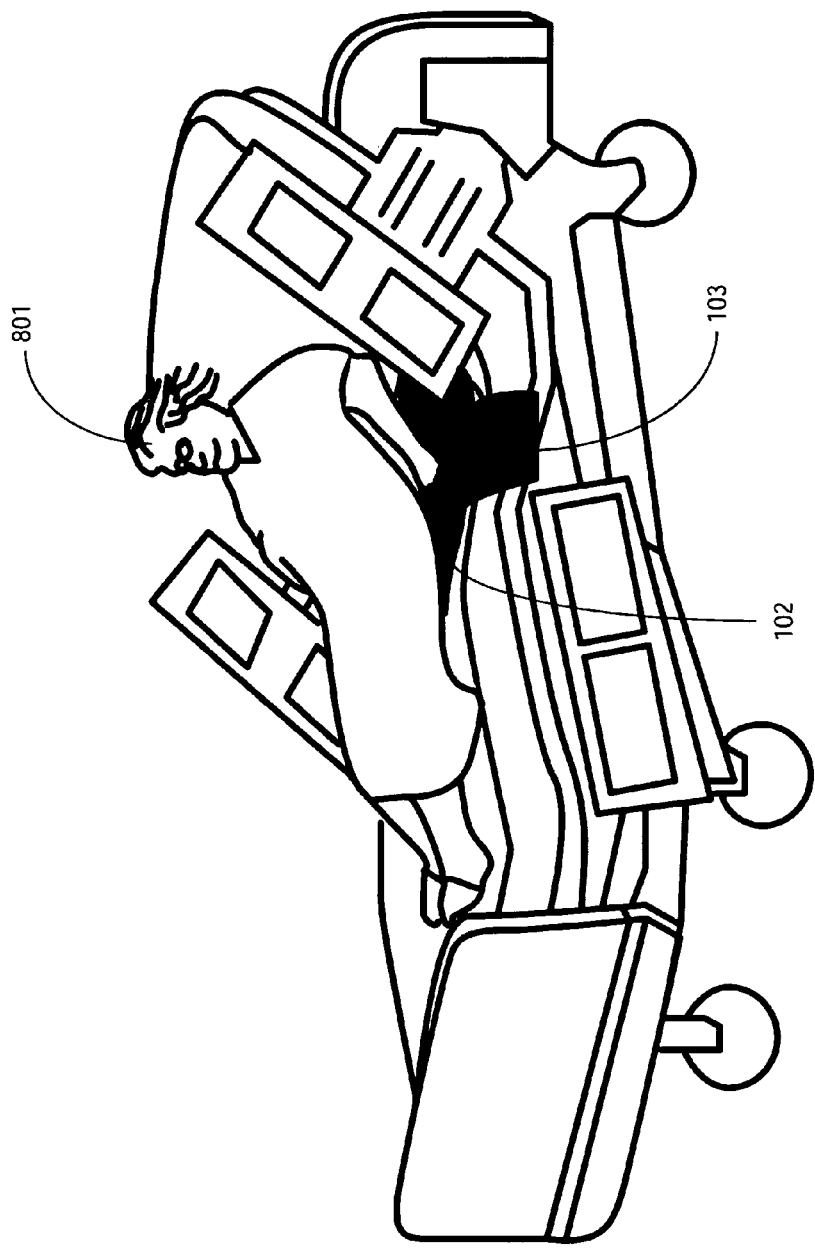

Turning now to FIGS. 7 and 8, illustrated therein is another application for a unitary patient monitoring system 100 in accordance with embodiments of the invention. The application illustrated in FIGS. 7 and 8 is that of an alarm to let caregivers know when a person has exited a bed 701. In such a configuration, the unitary patient monitoring system 100 can be configured in a larger shape and size than that of FIGS. 5 and 6, so as to generally match the mattress 702 of the bed 701. For example, the unitary patient monitoring system 100 may have a switch compartment 102 that is generally rectangular in shape and measures roughly the width of the bed by 24 to 36 inches in length.

As shown in FIGS. 7 and 8, the cover member 101 of the unitary patient monitoring system 100 is substantially T-shaped. A first portion of the T-shape, shown in FIG. 7 as the switch compartment 102, is placed along the mattress 702. A second portion of the T-shape, shown in FIG. 7 as the alarm compartment 103, can then hang down from the mattress 702. Specifically, as shown in FIG. 8, the alarm compartment 103 can hang substantially orthogonally from the switch compartment 102 beside the patient 801. The patient 801 is free to move or turn over without obstructing the alarm in the alarm compartment 103. Further, there are no wires with which to become tangled. Additionally, the caregiver has access to the alarm compartment 103 without having to move the patient.

Turning now to FIG. 9, illustrated therein is one method 900 of using a unitary patient monitoring system (100) in accordance with embodiments of the invention. The method 900 of FIG. 9 would be suitable, for instance, with the application shown in FIGS. 5 and 6.

At step 901, the caregiver obtains a unitary patient monitoring system (100). In one embodiment, this unitary patient monitoring system (100) will have a cover member (101) disposed about the system, and will include a loudspeaker (203) in an alarm region of the cover member (101), such as the switch compartment (102), and a weight sensitive switch (201) in a switch region of the cover member (101), such as the switch compartment (102).

At step 902, the caregiver opens any packaging in which the unitary patient monitoring system (100) was stored or shipped. Optional step 903 is used where the unitary patient monitoring system (100) includes a master switch (211). Specifically, where a master switch (211) is included, the caregiver switches on the master switch (211) at step 903. Where no master switch (211) is included, step 903 is omitted.

At step 904, the caregiver places the switch region of the unitary patient monitoring system (100) in the seat of a wheelchair or on the mattress of a bed. At step 905, the caregiver drapes the alarm region either off the mattress or between the seat and back of a wheelchair such that the alarm region dangles. By dangling, the alarm region of the unitary patient monitoring provides the caregiver with access to the alarm region and prevents the patient from obstructing or interfering with the alarm region.

At step 906, the caregiver assists or directs the patient onto the switch region of the unitary patient monitoring system (100), thereby causing the patient to sit or lie on the switch region. Where control circuitry (209) having auto-sensing functionality is included with the unitary patient monitoring system (100), the corresponding application of the patient's weight on the switch region activates the unitary patient monitoring system (100). When the patient removes his weight from the switch region, the alarm sounds.

Turning now to FIG. 10, illustrated therein is a method 1000 of using a unitary patient monitoring system (100) after the alarm has been actuated by the patient removing his weight from the switch region.

At step 1001, the alarm is sounding. At step 1002, the caregiver checks to see if the patient is okay. Once the patient's safety is taken care of, and where the unitary patient monitoring system (100) includes an interrupt switch (212), the caregiver may stop the alarm from sounding by pressing the interrupt switch (212) at step 1003.

At step 1004, the caregiver can reposition the unitary patient monitoring system (100). At step 1005, the caregiver can assist or direct the patient to place his weight back on the switch region, thereby reactivating the unitary patient monitoring system (100).

Turning now to FIG. 11, illustrated therein is a method 1100 of permitting a patient to remove himself from a unitary patient monitoring system (100) having an interrupt switch (212) in accordance with embodiments of the invention without setting off the alarm. Specifically, the method 1100 of FIG. 11 can be used, for example, where a patient needs to get up to go to the bathroom with the caregiver's assistance.

At step 1101, the caregiver causes the patient to apply his weight to the switch region of the unitary patient monitoring system (100) by sitting on the switch region or lying on the switch region. This application of weight causes the system to be actuated.

At step 1102, the caregiver actuates the interrupt switch (212) thereby preventing the alarm from sounding. At step 1103, the caregiver causes the patient to remove his weight from the switch region of the unitary patient monitoring system (100), perhaps by assisting the patient from the wheelchair or bed. At step 1104, the caregiver assists the patient with the necessary activity, be it going to the bathroom, exercising, eating a meal, or bathing. At step 11105, the caregiver assists the patient back onto the switch region of the unitary patient monitoring system (100), thereby resetting the alarm.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A unitary patient monitoring system, comprising:
a loudspeaker configured to emit an audible alarm upon actuation;
an energy source coupled to the loudspeaker;
a weight sensitive switch coupled between the energy source and the loudspeaker;
a master switch coupled with the loudspeaker and the energy source; and
a cover member encapsulating each of the loudspeaker, the master switch, the energy source, and the weight sensitive switch within the cover member.

2. The unitary patient monitoring system of claim 1, further comprising a control circuit coupled to and operable with the weight sensitive switch, wherein the control circuit is configured to actuate the loudspeaker only upon application, and successive removal, of at least a predetermined weight to the unitary patient monitoring system.

3. The unitary patient monitoring system of claim 2, wherein the control circuit is configured actuate the loudspeaker for one of a predetermined duration or a time period extending until the predetermined weight is applied to the weight sensitive switch.

4. The unitary patient monitoring system of claim 3, wherein the predetermined duration is between fifteen and sixty minutes.

5. The unitary patient monitoring system of claim 2, further comprising a interrupt switch operable with the control circuit, wherein the control circuit is configured to prevent the loudspeaker from emitting the audible alarm upon actuation of the interrupt switch until at least the predetermined weight is applied to, and removed from, the unitary patient monitoring system after the actuation of the interrupt switch.

6. The unitary patient monitoring system of claim 5, wherein the predetermined weight is 80 pounds.

7. The unitary patient monitoring system of claim 1, wherein the cover member defines a switch compartment and an alarm compartment extending from the switch compartment, wherein the weight sensitive switch is disposed within the switch compartment and the loudspeaker is disposed within the alarm compartment.

8. The unitary patient monitoring system of claim 7, wherein the weight sensitive switch is configured to actuate the loudspeaker when at least a predetermined weight is removed from atop the switch compartment.

9. The unitary patient monitoring system of claim 7, wherein the cover member comprises a sealed cover member having an antimicrobial coating.

10. The unitary patient monitoring system of claim 9, further comprising a removable, washable cover disposed about the sealed cover member.

11. The unitary patient monitoring system of claim 1, wherein the weight sensitive switch comprises a first electrical contact array and a second electrical contact array separated by a layer of compliant material, the compliant material being configured to permit at least a first electrical contact of the first electrical contact array to contact a second electrical contact of the second electrical contact array upon application of at least a predetermined force.

12. The unitary patient monitoring system of claim 1, wherein the audible alarm comprises an alarm of between 70 and 100 decibels.

13. The unitary patient monitoring system of claim 1, wherein the unitary patient monitoring system is disposable.

14. The unitary patient monitoring system of claim 1, wherein the loudspeaker is capable of actuation when the master switch is in a first position, and incapable of actuation when the master switch is in a second position.

15. A patient monitoring pad, comprising a T-shaped cover enclosing a loudspeaker, an energy source coupled to the loudspeaker, and a weight sensitive switch coupled between the energy source and the loudspeaker, wherein the loudspeaker is disposed in a first portion of the T-shaped cover and the weight sensitive switch is disposed in a second portion of the T-shaped cover extending from the first portion.

16. The patient monitoring pad of claim 15, wherein the first portion comprises a major face measuring between fourteen and eighteen inches in a first dimension and between sixteen and twenty inches in a second dimension, further wherein the first portion is larger than the second portion.

17. The patient monitoring pad of claim 15, wherein the T-shaped cover is sealed along a perimeter of the T-shaped cover.

18. A method of using a patient monitoring system having a cover member encapsulating a loudspeaker in an alarm region and a weight sensitive switch, operable with the loudspeaker, in a switch region, the method comprising the steps of:
   placing the switch region in a seat of a wheelchair; and
   draping the alarm region between the seat and a back of the wheelchair such that the alarm region dangles from the seat.

19. The method of claim 18, further comprising the steps of:
   causing a patient to sit on the switch region;
   actuating an interrupt switch disposed within the alarm region of the cover member; and
   causing the patient to remove from the switch region.

* * * * *